(12) United States Patent
Saito et al.

(10) Patent No.: US 11,198,893 B2
(45) Date of Patent: Dec. 14, 2021

(54) METHOD FOR PRODUCING OMEGA 3 AND OMEGA 6 UNSATURATED FATTY ACID OXIDES

(71) Applicant: Bizen Chemical Co., Ltd., Akaiwa (JP)

(72) Inventors: Shiho Saito, Akaiwa (JP); Yoshihisa Misawa, Akaiwa (JP); Naomichi Baba, Akaiwa (JP); Hiroshi Tabata, Akaiwa (JP); Tadahiro Tsushima, Akaiwa (JP); Jun Fujii, Akaiwa (JP)

(73) Assignee: Bizen Chemical Co., Ltd., Akaiwa (JP)

( * ) Notice: Subject to any disclaimer, the term of this patent is extended or adjusted under 35 U.S.C. 154(b) by 203 days.

(21) Appl. No.: 16/313,437

(22) PCT Filed: Jun. 19, 2017

(86) PCT No.: PCT/JP2017/022524
§ 371 (c)(1),
(2) Date: Dec. 26, 2018

(87) PCT Pub. No.: WO2018/003569
PCT Pub. Date: Jan. 4, 2018

(65) Prior Publication Data
US 2020/0140903 A1 May 7, 2020

(30) Foreign Application Priority Data
Jun. 30, 2016 (JP) .............................. JP2016-129796

(51) Int. Cl.
*C12P 7/64* (2006.01)
*A23L 33/12* (2016.01)
*A61K 31/232* (2006.01)

(52) U.S. Cl.
CPC ............. *C12P 7/6436* (2013.01); *A23L 33/12* (2016.08); *A61K 31/232* (2013.01)

(58) Field of Classification Search
CPC ..... A23L 33/12; A61K 31/202; A61K 31/232; A61K 36/48; A61P 3/04; A61P 3/10; A61P 9/10; C07C 51/47; C07C 59/42; C11C 3/06; C12P 7/6436; C12P 7/62; C12P 7/6427; C12P 7/6472; C12Y 113/11
See application file for complete search history.

(56) References Cited

U.S. PATENT DOCUMENTS

| | | | | |
|---|---|---|---|---|
| 5,464,761 A | | 11/1995 | Muller et al. | |
| 5,883,273 A | * | 3/1999 | Miller | ........................ C11B 3/12 554/167 |
| 2017/0022526 A1 | | 1/2017 | Ogawa et al. | |

FOREIGN PATENT DOCUMENTS

| | | |
|---|---|---|
| JP | 7-500252 A | 1/1995 |
| JP | 7-291862 A | 11/1995 |
| WO | 2015/063617 A2 | 5/2015 |
| WO | 2015/111699 A1 | 7/2015 |

OTHER PUBLICATIONS

Li et al., "Docosahexanoic Acid-Induced Coronary Arterial Dilation: Actions of 17S-Hydroxy Docosahexanoic Acid on $K^+$ Channel Activity," *The Journal of Pharmacology and Experimental Therapeutics* 336(3):891-899, 2011.

* cited by examiner

*Primary Examiner* — Blaine Lankford
(74) *Attorney, Agent, or Firm* — Seed IP Law Group LLP

(57) ABSTRACT

Provided is a method for producing an unsaturated fatty acid oxide (e.g. ω3 fatty acid oxide) that is new and has more beneficial features compared to conventional technologies. This method uses a lipoxygenase-containing composition (e.g. a lipoxygenase-containing composition derived from beans) as a lipoxygenase enzyme, and also uses a freezing method with organic solvent extraction. The present invention makes it possible to produce an unsaturated fatty acid oxide (e.g. ω3 fatty acid oxide) efficiently and at a low cost. The present invention also provides a pharmaceutical composition containing an ω3 fatty acid oxide isolated and purified by this method as an active ingredient.

10 Claims, No Drawings

METHOD FOR PRODUCING OMEGA 3 AND OMEGA 6 UNSATURATED FATTY ACID OXIDES

TECHNICAL FIELD

The present invention relates to a method of manufacturing ω3 and ω6 unsaturated fatty acid oxides.

BACKGROUND ART

Unsaturated fatty acids comprising two or more double bonds such as ω3 fatty acids, including EPA, DHA, and DPA, are converted to a fatty acid intermediate metabolite in the body to be involved in various physiological functions. It has been published that a reduction in the DHA oxidative metabolite, protectin D1, in the muscle and fat tissue is associated with obesity-linked chronic inflammation, and genetically recombinant mice capable of DHA synthesis can suppress insulin resistance due to obesity (Non Patent Literature 1). It is also published that the DHA oxidative metabolite protectin DX has action to suppress liver glucose synthesis and action to promote glycometabolism (Non Patent Literature 2).

It is reported that 17S-HDHA suppresses inflammatory cytokine expression to improve glucose tolerance and insulin resistance in an experiment using obese mice (Non Patent Literature 3).

17S-HDHA, which is expected to have a useful effect, has been confirmed to be present in organisms comprising a long chain ω3 polyunsaturated fatty acid such as fish, crustaceans, algae, and mollusks in nature. However, content of ω3 fatty acid oxides such as 17S-HDHA in nature is low, such that isolation from nature is not practical in terms of cost and labor.

ω3 fatty acid oxides can also be generated using an enzyme such as lipoxygenase (Patent Literature 1). However, this is problematic in that the enzyme itself is expensive and the efficiency of an enzyme reaction is not sufficient. A method of isolating/purifying a substance of interest from a reaction mixture after an enzyme reaction is still not sufficiently efficient.

CITATION LIST

Patent Literature

[PTL 1] WO 2015/063617

Non Patent Literature

[NPL 1] White et al., Transgenic restoration of long-chain n-3 fatty acids in insulin target tissues improves resolution capacity and alleviates obesity-linked inflammation and insulin resistance in high-fat-fed mice, Diabetes, 2010 December; 59(12): 3066-3073

[NPL 2] White et al., Protectin DX alleviates insulin resistance by activating a myokine-liver glucoregulatory axis, Nat. Med. 2014 June; 20(6): 664-669

[NPL 3] Neuhofer A et al., Impaired local production of proresolving lipid mediators in obesity and 17-HDHA as a potential treatment for obesity-associated inflammation, Diabetes 62: 1945-1956, 2013

SUMMARY OF INVENTION

Technical Problem

The problem to be solved of the present invention is to improve enzyme reaction conditions and a method of isolating/purifying a substance of interest from an enzyme reaction mixture in a method of generating, and then isolating/purifying an oxide (e.g., ω3 fatty acid oxide) of unsaturated fatty acid comprising two or more double bonds using an enzyme (e.g., lipoxygenase).

Solution to Problem

The inventors have enabled an efficient and economical lipoxygenase enzyme reaction for generating an oxide (e.g., ω3 fatty acid oxide) of unsaturated fatty acid comprising two or more double bonds by using a lipoxygenase containing composition (e.g., bean derived lipoxygenase containing composition), instead of an enzyme product, as a lipoxygenase enzyme. Examples of bean derived lipoxygenase containing compositions include, but are not limited to, bean flour and bean immersed solution prepared from beans (e.g., soybeans). The inventors have also used a freezing process instead of centrifugation for the isolation/purification of a product from a reaction solution (mixture) after an enzyme reaction to solve issues associated with the use of bean derived lipoxygenase containing composition to solve the above problem.

For example, the present invention provides the following.

(Item 1)

A method of manufacturing a modified form of unsaturated fatty acid comprising two or more double bonds or a modified form of an ethyl ester of unsaturated fatty acid comprising two or more double bonds, comprising:
(a) providing unsaturated fatty acid comprising two or more double bonds or an ethyl ester of unsaturated fatty acid comprising two or more double bonds;
(b) providing a mixture comprising a lipoxygenase containing composition and the unsaturated fatty acid or the ethyl ester of unsaturated fatty acid;
(c) incubating the mixture to perform an enzyme reaction;
(d) reducing the mixture generated in the enzyme reaction;
(e) adding an organic solvent to the reduced mixture;
(f) freezing the mixture after adding the organic solvent; and
(g) recovering a top layer of the mixture after freezing.

(Item 2)

The method of item 1, wherein the lipoxygenase containing composition is bean flour exhibiting lipoxygenase activity or bean immersed solution exhibiting lipoxygenase activity.

(Item 3)

The method of item 1, further comprising:
(h) dissolving the mixture after recovering the top layer in (g);
(i) adding an organic solvent to the mixture dissolved in (h);
(j) freezing the mixture after adding the organic solvent; and
(k) recovering a top layer of the mixture after freezing.

(Item 4)

The method of item 3, further comprising:
(l) dissolving the mixture after recovering the top layer in (k);
(m) adding an organic solvent to the mixture dissolved in step (l);
(n) freezing the mixture after adding the organic solvent; and
(o) recovering a top layer of the mixture after freezing.

(Item 5)

The method of item 1, wherein the unsaturated fatty acid is omega-3 based fatty acid.

(Item 6)

The method of item 5, wherein the omega-3 based fatty acid is selected from the group consisting of DHA, EPA, and DPA.

(Item 7)

The method of item 5, wherein the omega-3 based fatty acid is DHA.

(Item 8)

The method of item 1, wherein the lipoxygenase containing composition is soybean flour.

(Item 9)

The method of item 1, wherein the modified form of unsaturated fatty acid or the modified form of the ethyl ester of unsaturated fatty acid is 17S-HDHA or 17S-HDHA ethyl ester.

(Item 10)

A beverage composition comprising the modified form of unsaturated fatty acid or the modified form of the ethyl ester of unsaturated fatty acid manufactured by the method of item 1.

(Item 11)

A pharmaceutical composition comprising the modified form of unsaturated fatty acid or the modified form of the ethyl ester of unsaturated fatty acid manufactured by the method of item 1.

The present invention provides a method of manufacturing an unsaturated fatty acid oxide (e.g., ω3 fatty acid oxide). Examples of the unsaturated fatty acid oxide include, but are not limited to, oxidative metabolites of unsaturated fatty acid. For example, the present invention provides a method of manufacturing a substance selected from the group consisting of oxides of EPA, oxides of DPA, and oxides of DHA. For example, this oxide is selected from the group consisting of 17-HDHA, PDX, 17-HDPA, and 13-HSDA. EPA, DPA, and DHA are independently selected from the group consisting of free fatty acid forms, alcohol forms, ester forms, complexes with other physiological substances, various glyceride forms (e.g., monoglyceride, diglyceride, triglyceride, alkyl glyceryl ether lipid, alkenyl glyceryl ether lipid), various phospholipid forms (e.g., glycerophospholipid and sphingophospholipid), various amine salts (e.g., aliphatic amine salts such as trimethylamine salt, triethylamine salt, dicyclohexylamine salt, ethanolamine salt, diethanolamine salt, triethanolamine salt, procaine salt, meglumine salt, diethanolamine salt, or ethylenediamine salt; aralkylamine salts such as N,N-dibenzylethylenediamine salt and benethamine salt; and heterocyclic aromatic amine salts such as pyridine salt, picoline salt, quinoline salt, and isoquinoline salt), various ammonium salts (e.g., quaternary ammonium salts such as tetramethylammonium salt, tetraethylammonium salt, benzyltrimethylammonium salt, benzyltriethylammonium salt, benzyltributylammonium salt, methyltrioctylammonium salt, and tetrabutylammonium salt) and various metal salts (e.g., salts of lithium, sodium, potassium, cesium, rubidium, calcium, magnesium, aluminum, tin, zinc, lead, cobalt, and nickel). Furthermore, the alcohol moiety in ester form is selected from the group consisting of methanol, ethanol, propanol, isopropanol, butanol, and isomers thereof, pentanol and isomers thereof, hexanol and isomers thereof, heptanol and isomers thereof, octanol and isomers thereof, alcohol with a greater molecular weight (e.g., oleyl alcohol) and isomers thereof, and alcohol comprising an unsaturated bond and isomers thereof.

The composition comprising an oxide (e.g. ω3 fatty acid oxide) of unsaturated fatty acid comprising two or more double bonds of the invention also exhibits an excellent effect in the improvement (therapy and prevention) of insulin resistance, enhancement of insulin sensitivity, prevention and therapy of diabetes, improvement in glycometabolism, reduction of low density lipoprotein, reduction of cholesterol, reduction of obesity, prevention and therapy of hypertriglyceridemia, and prevention and therapy of atherosclerotic diseases.

Advantageous Effects of Invention

The present invention provides a method of manufacturing an oxide (e.g. ω3 fatty acid oxide) of unsaturated fatty acid comprising two or more double bonds, with new and better advantages compared to conventional technologies. The present invention enables efficient and cost-effective manufacture of ω3 fatty acid oxides.

DESCRIPTION OF EMBODIMENTS

The present invention is explained hereinafter. Throughout the entire specification, a singular expression should be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence. As used herein, "wt %" is interchangeably used with "mass percentage concentration". "%" refers to "wt %", "w/w %", or "mass percent concentration" unless specifically noted otherwise.

The definitions of the terms that are particularly used herein are listed hereinafter.

As used herein, the term "unsaturated fatty acid comprising two or more double bonds" refers to any unsaturated fatty acid comprising two or more double bonds, preferably fatty acid comprising double bonds at position ω3 and another position, and more preferably comprising double bonds at positions ω3 and ω6. The oxide of unsaturated fatty acid of the invention is preferably fatty acid to which one or more hydroxyl groups are bound to a specific position. Representative examples of unsaturated fatty acid comprising two or more double bonds include, but are not limited to, all fatty acids including n-3 and n-6 bases such as each of hexadecatrienoic acid, hexadecatetraenoic acid, linoleic acid, α-linolenic acid, γ-linolenic acid, stearidonic acid dihomo-γ-linolenic acid, eicosatetraenoic acid, arachidonic acid, eicosapentaenoic acid (EPA), docosadienoic acid, docosatrienoic acid, docosatetraenoic acid, docosapentaenoic acid (DPA), docosahexaenoic acid (DHA), tetracosapentaenoic acid, and tetracosahexaenoic acid. Examples of oxides of (modified form of) unsaturated fatty acid comprising two or more double bonds include, but are not limited to, 15-hydroxyeicosatetraenoic acid, 19-hydroxytetracosapentaenoic acid, 19-hydroxytetracosahexaenoic acid, 11-hydroxyhexadecatrienoic acid, 11-hydroxyhexadecatetraenoic acid, 13-hydroxylinoleic acid, 13-hydroxy-α-linolenic acid, 13-hydroxy-γ-linolenic acid, 13-hydroxystearidonic acid, 15-hydroxy-dihomo-γ-linolenic acid, 15-hydroxyeicosatetraenoic acid, 15-hydroxy EPA, 17-hydroxydocosadienoic acid, 17-hydroxydocosatrienoic acid, 17-hydroxydocosatetraenoic acid, 17-hydroxy DPA, 17-hydroxy DHA, 19-hydroxytetracosapentaenoic acid, and 19-hydroxytetracosahexaenoic acid.

As used herein, the term "ω3 fatty acid" refers to unsaturated fatty acid with a double bond from the third carbon (position ω3) from the methyl end. Representative examples thereof include, but are not limited to, α-linolenic acid, stearidonic acid, eicosatetraenoic acid, eicosapentaenoic acid (EPA), docosapentaenoic acid (DPA n-3), docosahexaenoic acid (DHA), tetracosapentaenoic acid, and tetracosahexaenoic acid.

As used herein, the term "modified form of ω3 fatty acid" is a substance from modifying ω3 fatty acid, including oxides (e.g., oxidative metabolites) of ω3 fatty acid. Representative examples thereof include, but are limited to, 13-hydroxy-α-linolenic acid, 13-hydroxystearidonic acid, 15-hydroxyeicosatetraenoic acid, 15-hydroxy EPA, 17-hydroxy DPAn-3, 17-hydroxy DHA, 19-hydroxytetracosapentaenoic acid, and 19-hydroxytetracosahexaenoic acid.

As used herein, the term "glyceride" encompasses components selected from the group consisting of triglyceride, diglyceride, and monoglyceride of fatty acid. In the present invention, "glyceride" does not encompass phospholipids or glycolipids, unless specified otherwise.

As used herein, the term "docosahexaenoic acid" is interchangeably used with "DHA", encompassing both the free fatty acid forms and forms having an ester bond with ethanol, glycerin, or phospholipid.

As used herein, the term "17-HDHA" refers to an oxide of DHA, which is a DHA in which position 17 is oxidized and bound to "—OH". The term "17-HDHA" is interchangeably used with the term "17-hydroxy DHA" and the term "17-hydroxydocosahexaenoic acid".

As used herein, the term "eicosapentaenoic acid" is interchangeably used with "EPA", encompassing both the free fatty acid forms and forms having an ester bond with ethanol, glycerin, or phospholipid.

As used herein, the term "docosapentaenoic acid" is interchangeably used with "DPA", encompassing both the free fatty acid forms and forms having an ester bond with ethanol, or glycerin. Further, "DPA" which is not specified as neither "n-3" nor "n-6" refers to "n-3 DPA" (i.e., all-cis-7,10,13,16,19-docosapentaenoic acid). "n-3 DPA" is interchangeably used with "ω-3 DPA".

As used herein, the term "17-HDPA" refers to an oxide of DPA, which is a DPA in which position 17 is oxidized and bound to "—OH".

As used herein, the term "n-6 DPA" Is interchangeably used with "all-cis-4,7,10,13,16-docosapentaenoic acid" or "ω6 DPA", encompassing both the free fatty acid forms and forms having an ester bond with ethanol or glycerin.

As used herein, the term "stearidonic acid" is interchangeably used with "SDA", encompassing both the free fatty acid forms and forms having an ester bond with ethanol or glycerin.

As used herein, the term "α-linolenic acid" is interchangeably used with "ALA", encompassing both the free fatty acid forms and forms having an ester bond with ethanol or glycerin.

As used herein, the term "eicosatetraenoic acid" is interchangeably used with "ETA", encompassing both the free fatty acid forms and forms having an ester bond with ethanol or glycerin.

As used herein, the term "lipoxygenase" refers to an oxidoreductase that adds molecular oxygen and introduces a hydroperoxy group to unsaturated fatty acid. The term lipoxygenase" is interchangeably used with "lipoxidase". "Lipoxygenase" is widely contained in plants. Examples of supply sources of lipoxygenase include, but are not limited to, beans (e.g., beans selected from the group consisting of soybeans, kidney beans, toramame (tiger beans), pinto beans, and green peas), tomatoes, cabbage, and *Arabidopsis thaliana*. A bean derived lipoxygenase containing composition can be used for an oxidation reaction by lipoxygenase in the present invention.

As used herein, the term "lipoxygenase containing composition" refers to a composition (liquid or solid) prepared from a plant (entire plant or part of a plant) containing lipoxygenase, comprising lipoxygenase contained in the raw material plant and at least one component other than lipoxygenase contained in the raw material plant. "Bean derived lipoxygenase containing composition" refers to a composition (liquid or solid) prepared from beans, comprising lipoxygenase contained in the raw material beans and at least one component other than lipoxygenase contained in the raw material beans. Examples of content of at least one component other than lipoxygenase contained in the raw material plant (e.g., beans) in a composition include, but are not limited to, 1% (w/w) or greater, 2% (w/w) or greater, 3% (w/w) or greater, 4% (w/w) or greater, 5% (w/w) or greater, 6% (w/w) or greater, 7% (w/w) or greater, 8% (w/w) or greater, 9% (w/w) or greater, 10% (w/w) or greater, 12% (w/w) or greater, 14% (w/w) or greater, 16% (w/w) or greater, 18% (w/w) or greater, or 20% (w/w). A composition prepared from a plant (e.g., beans) may be a liquid, solid, or contain both a liquid and solid. Examples of compositions prepared from beans include, but are not limited to, bean flour, bean immersed solution, and any composition comprising them.

As used herein, the term "bean flour" refers to powder obtained by grinding beans. Examples of beans include, but are not limited to, beans selected from the group consisting of soybeans, kidney beans, toramame (tiger beans), pinto beans, and green peas. The grinding conditions are not particularly limited. The particle size of ground beans is also not particularly limited. For example, ground products with a size of 600 μm to 2000 μm, 150 μm to 600 μm, or 150 μm or less and ground beans with a particle size of 2000 μm or greater can all be used. In the present invention, bean flour is preferably soybean flour.

As used herein, the term "soybean flour" refers to flour from grinding soybeans.

As used herein, the term "bean immersed solution" refers to a solution obtained from immersing beans in a liquid (e.g., water). Examples of beans include, but are not limited to, beans selected from the group consisting of soybeans, kidney beans, tiger beans, pinto beans, and green peas. The liquid can be aqueous or oily, and is preferably aqueous. Any liquid such as water of buffer can be used as the aqueous liquid. Immersion conditions are not particularly limited. Any condition can be used as long as a bean immersed solution exhibiting lipoxygenase activity is obtained. In the present invention, the bean immersed solution is preferably a soybean immersed solution.

As used herein, the term "freezing process" refers to a method of freezing an aqueous layer and emulsified intermediate layer to recover an organic solvent of the top layer, when adding the organic solvent to a reaction solution after an enzyme reaction to extract an oily component. The temperature at which the aqueous layer and intermediate layer are frozen can be appropriately determined by those skilled in the art in accordance with the composition and ratio of the organic solvent and enzyme reaction solution used. Examples of organic solvent include, but are not limited to, DHA ethyl ester, n-hexane, ethyl acetate, pentane, heptane, diethyl ether, and diisopropyl ether. Preferred organic solvents are n-hexane and DHA ethyl ester. The freezing process can be repeated multiple times, after recovering the top layer that is the organic solvent layer, by dissolving the frozen intermediate layer and adding an organic solvent thereto.

(Enzyme Reaction Utilizing Lipoxygenase Containing Composition)

"Lipoxygenase" that can be used in the present invention is widely contained in plants. Examples of supply sources of lipoxygenase include, but are not limited to, beans (e.g., beans selected from the group consisting of soybeans, kidney beans, toramame (tiger beans), pinto beans, and green peas), tomatoes, cabbage, and *Arabidopsis thaliana*. For example, the present invention can use a lipoxygenase containing composition (e.g., bean derived lipoxygenase containing composition) to perform a lipoxygenase enzyme reaction. Examples of bean-derived lipoxygenase containing composition include, but are not limited to, bean flour and bean immersed solution. Examples of beans used as a raw material include, but are not limited to, beans selected from the group consisting of soybeans, kidney beans, toramame (tiger beans), pinto beans, and green peas. Representative soybeans used for preparing the soybean flour or soybean immersed solution used in the present invention include, but are not limited to, seeds produced by legumes and soybeans. Examples of soybeans used include, but are not limited, common yellow soybeans as well as colored soybeans such as green soybeans and black soybeans.

The grinding conditions for preparing bean flour from beans are not particularly limited. The particle size of ground bean flour is also not particularly limited. For example, ground products with a size of 600 µm to 2000 µm, 150 µm to 600 µm, or 150 µm or less and ground beans with a particle size of 2000 µm or greater can all be used.

The grinding conditions for preparing soybean flour from soybeans are also not particularly limited. The particle size of ground soybean flour is also not particularly limited. For example, ground products with a size of 600 µm to 2000 µm, 150 µm to 600 µm, or 150 µm or less and ground beans with a particle size of 2000 µm or greater can all be used.

As the enzyme reaction conditions for using a lipoxygenase containing composition (e.g., bean derived lipoxygenase containing composition such as bean flour or bean immersed solution), any reactions conditions under which lipoxygenase enzyme contained in a lipoxygenase containing composition exhibits activity can be used. Examples of such enzyme reaction conditions include, but are not limited to the following. For example, bean flour such as soybean flour or bean immersed solution such as soybean immersed solution can be utilized as a bean-derived lipoxygenase containing composition. Alternatively, flour or immersed solution prepared from another bean can also be used instead of soybean flour or soybean immersed solution.

(1) Buffer used: boric acid buffer, ammonium water, or sodium acetate buffer (2) Temperature used: 30° C. or lower, preferably 0 to 5° C.

(3) Concentration of lipoxygenase containing composition used (e.g., bean derived lipoxygenase containing composition): typically 0.5% (w/w) to 1.0% (w/w); reaction is also possible thereabove or thereunder.

(4) Ratio of substrate and lipoxygenase containing composition (e.g., bean derived lipoxygenase containing composition): ratio of lipoxygenase containing composition (e.g., bean derived lipoxygenase containing composition) to substrate is desirably, but not limited to, 30% or less. For example, a reaction is also possible at 30% to 100% or 100% to 450%, or 450% or greater.

(5) Reaction time: 15 minutes to 6 hours is desirable, but can be 15 minutes or less or 6 hours or more.

Commercially available reagent lipoxygenase is sold under the specification of having lipoxygenase activity of 50,000 to 300,000 units/mg solids. Meanwhile, lipoxygenase activity of soybeans is 100 to 200 units/g solids, which is much lower compared to the reagent. For this reason, 250,000 to 3,000,000 times the weight of a lipoxygenase reagent would be required when soybeans are used for a reaction from the viewpoint of only the lipoxygenase activity values. However, experimental results have revealed that the same reaction can proceed with a much lower amount, i.e., amount of soybeans comprising enzymatic activity that is about 300-fold of enzymatic activity calculated from the amount of reagent.

For example, the ground beans can be readily removed from a reaction solution after completion of a reaction by using a mesh bag or cage-like container when adding ground beans (e.g., ground soybeans). Alternatively, when a bean immersed solution (e.g., soybean immersed solution) is added, a step of removing ground beans from the reaction solution can be omitted after the completion of a reaction because ground beans are removed in advance in a bean immersed solutions.

If the fatty acid oxide resulting from the above enzyme reaction is peroxide, the peroxide is reduced when needed to a hydroxide. Reduction can be performed by well-known means for converting peroxide, which is a reaction product, into hydroxide. As needed, reduction can be performed after purification or partial purification of peroxide from a reaction mixture. Examples of a reducing agent used include, but are not limited to, sodium borohydride, N-acetyl-L-cysteine, L-methionine, ascorbic acid, cystine, phosphorus based compounds, and sulfur compounds. Alternatively, a reducible tin compound such as tin chloride can be used as a reducing agent in the present invention. Examples of phosphorous based compounds include, but are not limited to, phosphines and phosphine derivatives (e.g., trimethylphosphine and triphenylphosphine). Examples of sulfur based compounds include, but are not limited to, compounds comprising a thiol group and compounds comprising a sulfide group. A natural product comprising a phosphorous based compound and/or sulfur based compound (e.g., onion, garlic, or the like) can also be used.

Prior to performing the following freezing process, the pH of an enzyme reactant (can be an enzyme reactant which has or has not been treated with a reducing agent) can be adjusted to about 4 to about 5 by adding an acidic substance such as citric acid.

(Freezing Process)

As used herein, the term "freezing process" refers to freezing emulsified intermediate layer and aqueous layer to recover an organic solvent of a top layer, when adding the organic solvent to a reaction solution after an enzyme reaction to extract oily components. The temperature at which the intermediate layer is frozen can be appropriately determined by those skilled in the art in accordance with the composition and ratio of the organic solvent and enzyme reaction solution used. The following is a representative example.

(1) Type of organic solvent used: organic solvent with a specific weight of 1.0 or less and a melting point of 0° C. or less can be typically used. Examples thereof include, but are not limited to, DHA ethyl ester, n-hexane, ethyl acetate, pentane, heptane, diethyl ether, and diisopropyl ether, and preferably n-hexane.

(2) Quantitative ratio of organic solvent used: preferably, but not limited to, 50% to 100% relative to the amount of solvent in the aqueous layer.
(3) Temperature used: 0° C. or less and preferably −20° C. or less (e.g., about −20° C., about −30° C., about −40° C., about −50° C., about −60° C., about −70° C., or about −80° C.)
(4) Freezing time: typically 30 minutes, but can be less than 30 minutes.

The preferred organic solvent is DHA ethyl ester. The freezing process can be repeated multiple times, after recovering the top layer that is the organic solvent layer, by dissolving the frozen intermediate layer and adding an organic solvent thereto. The preferred temperature conditions for such dissolving are a temperature that is higher than 0° C. and less than or equal to room temperature.

Although not wishing to be bound by any theory, freezing of moisture eliminates molecules other than water when water molecules form an aggregate with one another. For example, ice of saline, when frozen, hardly contains any salt component for this reason. A substance can be purified by recrystallization by the same principle. The present freezing process can quickly separate an aqueous layer and an organic solvent layer by utilizing this phenomenon.

With centrifugation, the interface between an oily layer and aqueous layer is unclear and soft, resulting in a large quantity of residuals to reduce the yield, whereas the use of the freezing process in the present invention clarifies the interface to enable efficient separation of an oily layer and an aqueous layer, resulting in improved yield (and purity).

The purity of the final product can be enhanced by applying the following well-known purification method to the top layer (organic solvent layer) recovered in this manner.

(Well-Known Purification Method)

*"Vacuum precision distillation" utilizes a difference in boiling point of each component for separation. For example for EPA, components with 20 carbon chains including EPA have an intermediate boiling point among fish oil fatty acid. The batch method requires the use of a single column distillation apparatus, while continuous distillation requires a two or four column apparatus. A two column apparatus performs purification by evaporating components of C19 or less (initial fraction) and sending the residual thereof to the second column to fractionate the C20 component (main fraction).

*"Fixed bed chromatographic method" provides and concentrates/purifies a fraction comprising a component of interest by filling a column with filler and allowing the raw material to pass therethrough with an eluent. Preferred filler include, but are not limited to, silica gel, reverse phase silica gel, and silver nitrate impregnated silica gel.

*"SMB chromatography" is a separation method utilizing the principle of liquid chromatography, using chromatography using a mobile phase forming an endless circulating system from linking multiple unit packed beds packed with an adsorbent having different selective adsorption capabilities between a specific components in the raw material and another specific component in series, and linking the most downstream unit packed bed with the most upstream unit packed bed. As used herein, "SMB chromatography" is interchangeably used with "simulated moving bed chromatography".

*"Winterization" is interchangeably used with "dewaxing", where oil and fat is maintained at a designated low temperature for a long period of time to elute oil and fat with a high melting point (e.g., glyceride or acylglycerol).

(Method of Preparing Raw Materials Used in the Method of the Invention)

For example, fish oil/crude oil ester can be used as EPA, DPA, and DHA, which are raw materials in the method of the invention.

An ethyl esterification method of a fraction comprising fatty acid is well known. For example, fatty acid in a fractionated glyceride fraction is ethyl esterified by an acidic catalyst or alkaline catalyst or an enzyme (lipase) in the presence of ethyl alcohol. Preferably, fatty acid in glycerin fatty acid ester contained in a fractionated glyceride fraction is ethyl esterified by the alkali catalyst method or enzymatic method. Fatty acid in a fractionated free fatty acid fraction is ethyl esterified by an acidic catalyst or an enzyme (lipase) in the presence of ethyl alcohol. When an enzyme is used, the amount of ethyl alcohol added is preferably an amount that does not inactivate the enzyme, and preferably, but not limited to, 4 mole equivalent or less and more preferably 2 mole equivalent or less to glyceride or free fatty acid.

Highly unsaturated fatty acid such as EPA and DHA in oil and fat comprising ethyl esterified ω3 based fatty acid is purified to a relatively high purity by a method combining one or more of urea addition method (Japanese Laid-Open Publication No. 2007-89522, Japanese National Phase PCT Laid-open Publication No. 2009-504588), silver nitrate complex method (Japanese Laid-Open Publication No. 2010-64974, Japanese Laid-Open Publication No. 7-242895), vacuum precision distillation including vacuum thin layer distillation method (Japanese Laid-Open Publication No. 11-209786), chromatographic methods such as liquid chromatography (hereinafter, referred to as HPLC) and simulated moving bed chromatographic method (Japanese Laid-Open Publication No. 11-209786), and the like. SMB chromatography can also be used. Representative purification methods are the following.

(1. Urea Addition Method)

Urea addition method is a purification method utilizing the property of forming a hexagonal prism-like adduct crystal while taking in straight chain molecules when dissolved urea is crystallized. For example, a raw material and a urea methanol solution are mixed and cooled to form a urea adduct incorporating monounsaturated fatty acid or saturated fatty acid, which is filtered out for purification. Typically, the urea adduct is subjected to n-hexane extraction and treated with silica gel, and then n-hexane is evaporated to obtain the unsaturated fatty acid of interest.

(2. Silver Nitrate Complex Method)

Silver nitrate complex method is a purification method utilizing the property of a silver nitrate solution forming a complex to a double bond of fatty acid. When a highly unsaturated fatty acid ethyl ester is purified, the highly unsaturated fatty acid ethyl ester of interest is concentrated/purified by agitating a raw material and a silver nitrate solution, subjecting unreacted ester to, for example, n-hexane extraction, then diluting or heating the aqueous phase, and extracting the free ester again with n-hexane.

(3. Vacuum Precision Distillation)

Vacuum rectification is a separation method utilizing a difference in boiling point of each component. For EPA, components with 20 carbon chains including EPA have an intermediate boiling point among fish oil fatty acid. The batch method requires the use of a single column distillation apparatus, while continuous distillation requires a two or four column apparatus. A two column apparatus performs purification by evaporating out components of C19 or less (initial fraction) and sending the residual thereof to the second column to fractionate the C20 component (main fraction).

(4. Chromatographic Method)

Chromatographic method includes a method using fixed bed chromatography (fixed bed chromatographic method) and SMB chromatographic method (simulated moving bed chromatographic method). Fixed bet chromatographic method is a method of extracting and concentrating/purifying a fraction comprising a component of interest by filling a column with filler and allowing the raw material to pass therethrough with an eluent. Preferred filler in the method of the invention include, but are not limited to, silica gel, reverse phase silica gel, and silver nitrate impregnated silica gel.

(5. SMB Chromatography)

SMB chromatography supplies a raw material and an eluent to an endless circulating system, and extracts component X moving at a high speed in the column (unit packed bed) (i.e., low affinity component) and component Y moving at a low speed in the column (i.e., component with affinity) at different positions. SMB chromatography materializes simulation of continuous operation of supplying raw material by sequentially moving the raw material supplying position, eluent supplying position, component X extraction position, and component Y extraction position downstream in the direct of the fluid circulation while maintaining a certain positional relationship. This is an operational method that can, as a result, move the distribution of each component in the layers at nearly r constant width, so that it is possible to continue to take a portion with high purity/concentration and the position of extraction of each component.

(Pharmaceutical Composition)

The present invention provides a composition comprising an oxide (e.g., ω3 fatty acid oxide) of unsaturated fatty acid comprising two or more double bonds, which is excellent for the prevention and therapy of diabetes, enhancement of insulin sensitivity, improvement in glycometabolism, reduction of low density lipoprotein, reduction of cholesterol, and prevention and therapy of obesity, hypertriglyceridemia, atherosclerotic diseases and diseases associated therewith.

For example, the pharmaceutical composition of the invention is a pharmaceutical composition for an application selected from the group consisting of therapy and prevention of insulin resistance, enhancement of insulin sensitivity, prevention and therapy of diabetes, improvement in glycometabolism, reduction of low density lipoprotein, reduction of cholesterol, reduction of obesity, prevention and therapy of hypertriglyceridemia, and prevention and therapy of atherosclerotic diseases.

(Formulation of Pharmaceutical Composition)

The present invention also provides a method of treating and/or preventing a disease or disorder that can be treated and/or prevented by administrating an effective amount of a therapeutic agent to a subject. A therapeutic agent refers to the composition of the invention combined with a pharmaceutically acceptable carrier form (e.g., sterilized carrier).

A therapeutic agent is prescribed and administered in a manner in compliance with GMP (good medical practice) by considering the clinical status of individual patients (especially side effects from treatment with a therapeutic agent alone), delivery site, administration method, dosing regimen, and other factors known to those skilled in the art. Therefore, the "effective amount" of interest herein is determined while taking them into consideration.

A preferred dosage form of the pharmaceutical composition of the invention is oral administration, but parenteral administration can also be used. In one embodiment, a therapeutic agent is generally prescribed, at a desired level of purity, mixed with a pharmaceutically acceptable carrier, i.e., carrier without toxicity to a recipient at a dosage and concentration used and compatible with other components in a formulation, in an injectable form in a unit dose (solution, suspension, or emulsion) for parenteral administration. For example, this formulation is preferably free of other compounds known to be detrimental for oxidation or therapeutic agent.

The formulation of the invention is a liquid or semi-solid (i.e., exhibiting a melting point range higher than room temperature) and can be orally administered to a patient in need thereof using a medicinal dosage form that is known to those skilled in the art. In particular, such a medicinal dosage form can be a hard shell capsule or a soft gel capsule. Such a capsule includes hard gelatin capsules and soft gelatin capsules. The formulation can also be converted into a conventional solid dosage form by a technique known to those skilled in the art such as adsorption or hot melt granulation/coating and/or with a select carrier, diluent, additive and/or binding agent.

A modified form of unsaturated fatty acid comprising two or more double bonds or a modified form of ethyl ester of unsaturated fatty acid comprising two or more double bonds manufactured by the present invention can also be used in a form of a medicinal formulation as a mixture with a pharmaceutically acceptable carrier such as a solid or liquid organic or inorganic excipient suitable for oral or parenteral administration or external application, including topical, enteral, intravenous, intramuscular, inhalation, nasal, intraarticular, intraspinal, transtracheal, and transocular administration. Examples of the medicinal formulations include solids, semi-solids, and liquids such as a capsule, tablet, pellet, sugar-coated tablet, powder, granule, suppository, ointment, cream, lotion, inhalant, injection, plaster, gel, tape, eye drop, liquid agent, syrup, aerosol, suspension, and emulsion. These formulations can be manufactured by a common method. When desired, an auxiliary, stabilizer, humectant or emulsifier, buffer, or other conventional additive can be added to these formulations.

A modified form of unsaturated fatty acid comprising two or more double bonds or a modified form of an ethyl ester of unsaturated fatty acid comprising two or more double bonds manufactured by the present invention can also be administered through any suitable route including, for example, topical administration through the nose with a nasal spray, transtracheally with an inhalant, or rectally with a suppository, or tablets, powder, or ointment.

In general, a preparation is prepared by homogeneously and closely contacting a therapeutic agent with a liquid carrier, microsectioned solid carrier, or both. If necessary, a product is then molded into a desired preparation. Preferably, a carrier is a parenteral carrier and more preferably a solution that is isotonic with blood of a recipient. Examples of such a carrier vehicle include water, saline, Ringer's solution, and dextrose solution. Nonaqueous vehicles such as nonvolatile oil and ethyl oleate can also be useful herein just like a liposome.

A carrier suitably contains a minute amount of an additive such as a substance increasing isotonicity and chemical stability. Such a substance does not have toxicity to a recipient at a dosage and concentration used. Examples of such a substance include: buffers such as phosphate, citrate, succinate, acetic acid and other organic acids and salts thereof; antioxidants such as ascorbic acid; low molecular weight (less than about 10 residues) polypeptides (e.g., polyarginine or tripeptide); proteins such as serum albumin, gelatin, or immunoglobulin; hydrophilic polymers such as polyvinylpyrrolidone; amino acids such as glycine, glutamic acid, aspartic acid, or arginine; cellulose or derivatives thereof; monosaccharides and disaccharides including glucose, mannose, and dextrin, and other carbohydrates; chelating agents such as EDTA; sugar alcohol such as mannitol or sorbitol; counterions such as sodium; and/or non-ionic surfactants such as polysorbate, poloxamer, or PEG.

Any agent to be used in therapeutic administration can be free of an organism/virus other than the virus used as an active ingredient, i.e., aseptic. An aseptic condition can be readily attained by filtration through a sterile filtration membrane (e.g., 0.2 micron membrane). In general, a therapeutic agent is placed in a container with a sterile access port, e.g., i.v. intravenous solution bag or vial with a stopper that can be punctured with a hypodermic needle.

A therapeutic agent can be stored in a single dose or multiple dose container such as a sealed ampule or vial as an aqueous solution or a lyophilized preparation for reconstitution. As an example of a lyophilized preparation, 5 ml of sterile filtered aqueous 5% (w/v) therapeutic solution is filled in a 10 ml vial, and the resulting mixture is lyophilized. The lyophilized therapeutic agent can be reconstituted using a bacteriostatic water for injection to prepare an injection solution.

The present invention also provides a pharmaceutical pack or kit comprising one or more containers filled with one or more components of the therapeutic agent of the invention. A notice in a form stipulated by the government agency restricting the manufacture, use, or sale of pharmaceutical products or biological products can be affixed to such a container. Such a notice indicates an approval by the government agency for the manufacture, use, or sale for administration to humans. A therapeutic agent can also be used in combination with another therapeutic compound.

The therapeutic agent of the invention can be administered alone or in combination with another therapeutic agent. A combination can be administered, for example, simultaneously as a mixture; simultaneously or in parallel, but separately; or sequentially. This includes an indication to coadminister combined agents as a therapeutic mixture and a procedure to administer combined agents separately but simultaneously such as through separate intravenous lines in the same individual. "Combined" administration further includes separate administration of one of the compounds or agents, which are given first followed by the second.

(Manufacture of Dietary Composition)

A preferable embodiment of the invention is a dietary composition. In other words, a pharmaceutical composition or dietary composition comprising the ω3 fatty acid oxides of the invention as an active ingredient can be directly added to liquid, gel, or solid food products such as juice, soft drink, coffee, tea, Japanese tea, oolong tea, vegetable juice, natural fruit juice, milk drink, milk, soy milk, sports drink, near water beverage, nutrition supplement beverage, coffee drink, cocoa, soup, dressing, mousse, jelly, yogurt, pudding, furikake seasoning, nursery powdered milk, processed milk, sports drink, nutrition drink, cake mix, bread, pizza, pie, cracker, biscuit, cake, cookie, spaghetti, macaroni, pasta, udon, soba, ramen, candy, soft candy, gum, chocolate, rice cracker, potato chips, snacks, ice cream, sherbet, cream, cheese, powdered or liquid dairy products such as powdered milk, condensed milk, and milk drink, manju, uiro, mochi, ohagi, soy sauce, dipping sauce, noodle sauce, sauce, stock, stew stock, soup stock, compound seasoning, curry sauce stock, mayonnaise, ketchup, instant curry, instant stew, instant soup, instant rice bowl, canned food, ham, Hamburg steak, meatball, croquettes, dumplings, pilaf, rice ball, frozen food and refrigerated food, chikuwa, fish paste, rice in boxed lunch, sushi, infant formula, weaning food, baby food, sports food, nutritional supplement, supplement, or health food, or processed into a pellet, tablet, granule, or the like with dextrin, lactose, starch, or other excipient, flavor, dye or the like as needed, or covered with gelatin or the like to be molded into a capsule for use as a health food, nutrition supplement or the like. Examples of the amount of ω3 fatty acid oxide added in such a food product or dietary composition include, but are not limited to, 3% (w/w) to 50% (w/w), 5% (w/w) to 40% (w/w), 10% (w/w) to 30% (w/w), and 15% (w/w) to 25% (w/w). Examples of the amount of DHA added in such a food product or dietary composition include, but are not limited to, 20% (w/w) to 80% (w/w), 30% (w/w) to 70% (w/w), 40% (w/w) to 60% (w/w), and 45% (w/w) to 55% (w/w). The amount of unsaturated fatty acid oxide added when used in supplements or the like is typically 0.1% to 10% or greater.

When the composition of the invention is used as a supplement, the active ingredient can be used directly, or administered after formulating the active ingredient into a soft capsule, tablet, powder, granule, or the like. When the composition of the invention is used in a dietary products, the composition can be administered by adding the composition to the ingredient of the dietary products.

EXAMPLES

While the present invention is explained hereinafter in more detail with the Examples and the like, the present invention is not limited thereto.

Example 1

17S-HDHA was manufactured and recovered from DHA using the following method.

(1) DHA (10.0 g; 0.030 mol) is dissolved in 300 mL of 0.024 M ammonia water.

(2) 20 mg of antifoaming agent is added thereto and the reaction solution is cooled to 0 to 5° C.

(3) After checking the temperature, 2 g of ground soybeans is placed in a nonwoven fabric filter and added to the reaction solution.

(4) Oxygen is blown in at least at 0.005 MPa.

(5) The reaction solution is agitated at 0 to 5° C. for 1 hour at 150 rpm.

(6) Some of the reaction solution is collected to check the reaction by TLC.

(7) If unreacted DHA is found, the reaction is continued for another 30 minutes to 5 hours.

(8) After completion of the reaction, oxygen blowing is discontinued, and a reducing agent N-acetyl-1-cysteine (19.6 g; 0.120 mol) is added and agitated for 45 minutes for reduction.

(9) The reaction solution is then adjusted to a pH of about 4 to about 5 with citric acid.

(10) 100 mL of n-hexane is added and the solution is agitated by inverted mixing, and then left standing until the intermediate layer coagulates in a freezer at −50° C.

(11) After recovering the top layer, 100 mL of n-hexane is added when the bottom layer melts, and the mixture is frozen under the same conditions. This operation is repeated three times.

(12) After washing the recovered solution after freezing with saturated saline solution and pure water, the solution is dehydrated with anhydrous $MgSO_4$.
(13) After filtration of the solution, the solvent is evaporated to recover 6.80 g of oil containing 17S-HDHA of interest.

Use of the above method of the invention resulted in attaining an excellent effect of improving the recovery rate of oil containing 17S-HDHA 2-fold or greater relative to conventional methods.

Although not wishing to be bound by any theory, precipitation of protein eluted from soybeans becomes problematic when the reaction solution prior to the extraction step leans from alkaline to acidic in an oxidation reaction using soybeans, but an intermediate layer comprising insoluble proteins appears between the top layer and the aqueous layer when mixing an organic solvent with a reaction solution comprising the precipitated protein. This is a phenomenon that is observed more notably when the particle size of soybeans is smaller. Centrifugation used in conventional methods does not sufficiently immobilize the intermediate layer strongly, such that the recovery rate of oil decreases. In this regard, use of the freezing process of the invention characterized by immobilizing the intermediate layer comprising insoluble proteins results in significant improvement in the recovery rate.

The present invention has been exemplified above using preferred embodiments of the invention, but the present invention should not be interpreted to be limited to the embodiment. In other words, compositions that can be used as the lipoxygenase containing composition of the invention is not limited to soybean flour, where flour derived from beans other than soybeans. (beans containing lipoxygenase) can also be used. As a composition that can be used as the bean derived lipoxygenase containing composition of the invention, bean immersed solution (e.g., soybean immersed solution) can also be used. It is also understood that the scope of the present invention should be interpreted solely from the scope of Claims. It is understood that those skilled in the art can implement an equivalent scope from the descriptions of the specific preferred embodiments of the invention based on the description of the present invention and common general knowledge. It is understood that any patent, any patent application, and any references cited herein should be incorporated herein by reference in the same manner as the contents are specifically described herein.

INDUSTRIAL APPLICABILITY

The present invention provides a method of manufacturing an ω3 fatty acid oxide with new and better advantages relative to conventional technologies. The present invention enables efficient and cost-effective manufacture of ω3 fatty acid oxides.

The invention claimed is:
1. A method of manufacturing a fatty acid hydroxide of an unsaturated fatty acid comprising two or more double bonds, or a fatty acid hydroxide of an ethyl ester of an unsaturated fatty acid comprising two or more double bonds, comprising:
(a) providing an unsaturated fatty acid comprising two or more double bonds or an ethyl ester of an unsaturated fatty acid comprising two or more double bonds;
(b) mixing an aqueous lipoxygenase-containing composition and the unsaturated fatty acid or the ethyl ester of unsaturated fatty acid of (a) to obtain a mixture comprising the lipoxygenase-containing composition and the unsaturated fatty acid or the ethyl ester of unsaturated fatty acid;
(c) incubating the mixture of (b) to perform an enzyme reaction to produce a fatty acid peroxide in an enzyme reaction mixture;
(d) reducing with a reducing agent the fatty acid peroxide in the enzyme reaction mixture of (c) into a fatty acid hydroxide, to obtain a first reduced enzyme reaction mixture;
(e) adding an organic solvent to the first reduced enzyme reaction mixture comprising the fatty acid hydroxide of (d);
freezing the first reduced enzyme reaction mixture comprising the fatty acid hydroxide of (d) after the step (e) of adding the organic solvent, to obtain a frozen aqueous layer, a frozen emulsified intermediate layer and a first recoverable top layer comprising the organic solvent and the fatty acid hydroxide; and
(g) after the step (f) of freezing, recovering the first recoverable top layer comprising the organic solvent and the fatty acid hydroxide, and thereby manufacturing the fatty acid hydroxide of said unsaturated fatty acid comprising two or more double bonds, or the fatty acid hydroxide of said ethyl ester of an unsaturated fatty acid comprising two or more double bonds.

2. The method of claim 1, wherein the lipoxygenase containing composition is bean flour exhibiting lipoxygenase activity or bean immersed solution exhibiting lipoxygenase activity.

3. The method of claim 1, further comprising:
(h) after step (g), melting the frozen aqueous and emulsified intermediate layers of the first reduced enzyme reaction mixture to obtain a second reduced enzyme reaction mixture comprising a fatty acid hydroxide;
(i) adding an organic solvent to the second reduced enzyme reaction mixture comprising the fatty acid hydroxide obtained in (h);
(j) freezing the second reduced enzyme reaction mixture comprising the fatty acid hydroxide obtained in (h) after the step (i) of adding the organic solvent to obtain a second frozen aqueous layer, a second frozen emulsified intermediate layer and a second recoverable top layer comprising the organic solvent and the fatty acid hydroxide obtained in (h); and
(k) after the step of freezing in (j), recovering the second recoverable top layer comprising the organic solvent and the fatty acid hydroxide.

4. The method of claim 3, further comprising:
(l) after step (k), melting the second frozen aqueous layer and the second frozen emulsified intermediate layer of the second reduced enzyme reaction mixture, to obtain a third reduced enzyme reaction mixture comprising a fatty acid hydroxide;
(m) adding an organic solvent to the third reduced enzyme reaction mixture comprising the fatty acid hydroxide obtained in step (l);
(n) freezing the third reduced enzyme reaction mixture comprising the fatty acid hydroxide obtained in (l) after the step (m) of adding the organic solvent to obtain a third frozen aqueous layer, a third frozen emulsified intermediate layer and a third recoverable top layer comprising the organic solvent and the fatty acid hydroxide obtained in (l); and
(o) after the step of freezing in (n), recovering the third recoverable top layer comprising the organic solvent and the fatty acid hydroxide.

5. The method of claim 1, wherein the unsaturated fatty acid is omega-3 based fatty acid.

6. The method of claim 5, wherein the omega-3 based fatty acid is selected from the group consisting of DHA, EPA, and DPA.

7. The method of claim 5, wherein the omega-3 based fatty acid is DHA.

8. The method of claim 1, wherein the lipoxygenase containing composition is soybean flour.

9. The method of claim 1, wherein the fatty acid hydroxide of unsaturated fatty acid or the fatty acid hydroxide of the ethyl ester of unsaturated fatty acid is 17S-HDHA or 17S-HDHA ethyl ester.

10. The method of claim 1 wherein steps (e), (f), and (g) are repeated three times.

* * * * *

UNITED STATES PATENT AND TRADEMARK OFFICE
CERTIFICATE OF CORRECTION

| | | |
|---|---|---|
| PATENT NO. | : 11,198,893 B2 | Page 1 of 1 |
| APPLICATION NO. | : 16/313437 | |
| DATED | : December 14, 2021 | |
| INVENTOR(S) | : Shiho Saito et al. | |

It is certified that error appears in the above-identified patent and that said Letters Patent is hereby corrected as shown below:

In the Claims

Column 16, Claim 1, Line 14:
"freezing the first reduced enzyme" should read: --(f) freezing the first reduced enzyme--.

Signed and Sealed this
Twenty-third Day of May, 2023

Katherine Kelly Vidal
*Director of the United States Patent and Trademark Office*